United States Patent
Kobayashi et al.

(10) Patent No.: US 7,850,598 B2
(45) Date of Patent: Dec. 14, 2010

(54) ENDOSCOPE APPARATUS FOR PERFORMING MEASUREMENT USING IMAGE

(75) Inventors: Eiichi Kobayashi, Tama (JP); Hideyoshi Yamauchi, Hino (JP)

(73) Assignee: Olympus Corporation, Tokyo (JP)

( * ) Notice: Subject to any disclaimer, the term of this patent is extended or adjusted under 35 U.S.C. 154(b) by 732 days.

(21) Appl. No.: 11/314,666

(22) Filed: Dec. 21, 2005

(65) Prior Publication Data

US 2006/0161042 A1   Jul. 20, 2006

(30) Foreign Application Priority Data

Dec. 27, 2004   (JP)   ............................. 2004-378012
Dec. 8, 2005    (JP)   ............................. 2005-355170

(51) Int. Cl.
    *A61B 1/04* (2006.01)
(52) U.S. Cl. .......................... 600/109; 600/118; 348/65
(58) Field of Classification Search ................ 600/109, 600/111, 118, 166; 348/65, 74, 76
    See application file for complete search history.

(56) References Cited

U.S. PATENT DOCUMENTS

| | | | | |
|---|---|---|---|---|
| 5,260,871 A | * | 11/1993 | Goldberg | ..................... 600/320 |
| 6,063,023 A | * | 5/2000 | Sakiyama et al. | ........... 600/118 |
| 6,120,435 A | * | 9/2000 | Eino | ........................... 600/118 |
| 6,717,609 B2 | * | 4/2004 | Sugimoto et al. | ............. 348/74 |
| 6,840,296 B2 | * | 1/2005 | Suzuki et al. | .......... 152/209.17 |
| 6,945,930 B2 | * | 9/2005 | Yokota | ....................... 600/118 |
| 2002/0183590 A1 | * | 12/2002 | Ogawa | ....................... 600/117 |
| 2003/0060681 A1 | * | 3/2003 | Yokota | ....................... 600/117 |
| 2004/0019253 A1 | * | 1/2004 | Tsujita et al. | ............... 600/118 |
| 2004/0191074 A1 | * | 9/2004 | Kajita | ..................... 417/199.1 |

FOREIGN PATENT DOCUMENTS

JP   10-248806   9/1998

* cited by examiner

*Primary Examiner*—John P Leubecker
*Assistant Examiner*—Samuel Candler
(74) *Attorney, Agent, or Firm*—Scully, Scott, Murphy & Presser, P.C.

(57) ABSTRACT

A CPU includes: an original image recording function for recording a still image or a recorded image as an original image; a contrast correction function for performing contrast correction on a still image or a recorded image; a coordinate calculation function for calculating pixel coordinates on an original image which correspond to pixel coordinates designated on a contrast corrected image; a stereo measurement function for performing stereo measurement using pixel coordinates of an original image calculated by the coordinate calculation function; a measurement result reflection function for reflecting on a contrast corrected image a measurement result of stereo measurement performed by the stereo measurement function; and a dynamic range expansion function for enhancing brightness of an image area which is darker than a predetermined threshold. These functions enable stereo measurement to be performed precisely using an image on which image processing has been performed.

10 Claims, 17 Drawing Sheets

FIG.10

STILL IMAGE
OR
RECORDED
IMAGE

CNT LEVEL  1 ■  □  □ 3

2004/09/09 12:00    001

ENDOSCOPE APPARATUS FOR PERFORMING MEASUREMENT USING IMAGE

This application claims benefit of Japanese Application No. 2004-378012 filed in Japan on Dec. 27, 2004, and Japanese Application No. 2005-355170 filed in Japan on Dec. 8, 2005, the contents of which are incorporated by this reference.

BACKGROUND OF THE INVENTION

1. Field of the Invention

The present invention relates to an endoscope apparatus in which images of an object to be measured, which are taken by a plurality of objective optical systems, are formed at different positions on an image pickup element provided in an endoscope and in which measurement is performed using the images.

2. Related Art Statement

A first example of a related art endoscope apparatus for use in measurement is disclosed, for example, in Japanese Unexamined Patent Application Publication No. 10-248806.

In this example, each image taken by a plurality of objective optical systems provided in a distal end of an insertion section is formed as it is on an image pickup element, and correction of optical distortion is performed for each of the optical systems.

OBJECTS AND SUMMARY OF THE INVENTION

An endoscope apparatus according to the present invention includes:

an endoscope for picking up images from different visual points;

an image generating portion for generating an endoscope image from a picked-up image signal picked up by the endoscope;

an image recording/reproducing portion for recording on a recording portion a still image, as a recorded image, obtained by freeze-framing the endoscope image as well as reading out the recording image from the recording portion;

an original image recording portion for temporarily recording the still image or the recorded image as an original image;

an image correcting portion for performing image correction on the still image or the recorded image;

a measurement point designating portion for designating a stereo measurement point on a corrected image on which image correction has been performed by the image correcting portion; and a stereo measurement portion for calculating a corresponding measurement point on the original image, which corresponds to the stereo measurement point on the corrected image, and performing stereo measurement using the corresponding measurement point of the original image.

Other features and advantages of the present invention will be readily apparent from the following description.

BRIEF DESCRIPTION OF THE DRAWINGS

FIG. 1 through FIG. 18 are related to an Embodiment 1 of the present invention:

FIG. 1 is an appearance diagram showing an appearance of an endoscope apparatus;

FIG. 2 is a block diagram showing a configuration of the endoscope apparatus of FIG. 1;

FIG. 3 is a diagram showing a configuration of a distal end of the endoscope of FIG. 1;

FIG. 4 is a functional block diagram showing functions of substantial portions of the CPU of FIG. 2;

FIG. 5 is a flowchart illustrating a first operation process of the CPU of FIG. 4;

FIG. 6 is a flowchart illustrating a second operation process of the CPU of FIG. 4;

FIG. 7 is a flowchart illustrating the live image display processing of FIG. 5 or FIG. 6;

FIG. 8 is a diagram showing a brightness indicator superimposed on an LCD in the processing of FIG. 7;

FIG. 9 is a first flowchart illustrating the still image display processing of FIG. 5 or the recorded image display processing of FIG. 6;

FIG. 10 is a diagram showing a contrast indicator superimposed on the LCD in the processing of FIG. 9;

FIG. 11 is a flowchart illustrating the contrast correction processing of FIG. 9:

FIG. 12 is a flowchart illustrating the corrected image recording processing of FIG. 9;

FIG. 13 is a first flowchart illustrating the still image display processing of FIG. 5 or the recorded image display processing of FIG. 6 when stereo measurement is instructed;

FIG. 14 is a diagram showing a functional configuration of the video processing circuit of FIG. 2 for implementing a dynamic range expansion function;

FIG. 15 is a diagram showing state transitions of dynamic range correction performed in response to depressions of the dynamic range correction switch of FIG. 1;

FIG. 16 is a diagram showing a dynamic range indicator, etc. superimposed on the LCD in the state transition of FIG. 15;

FIG. 17 is a second flowchart illustrating the still image display processing of FIG. 5 or the recorded image display processing of FIG. 6; and FIG. 18 is a second flowchart illustrating the still image display processing of FIG. 5 or the recorded image display processing of FIG. 6 when stereo measurement is instructed.

DETAILED DESCRIPTION OF THE PREFERRED EMBODIMENTS

Figure 1:
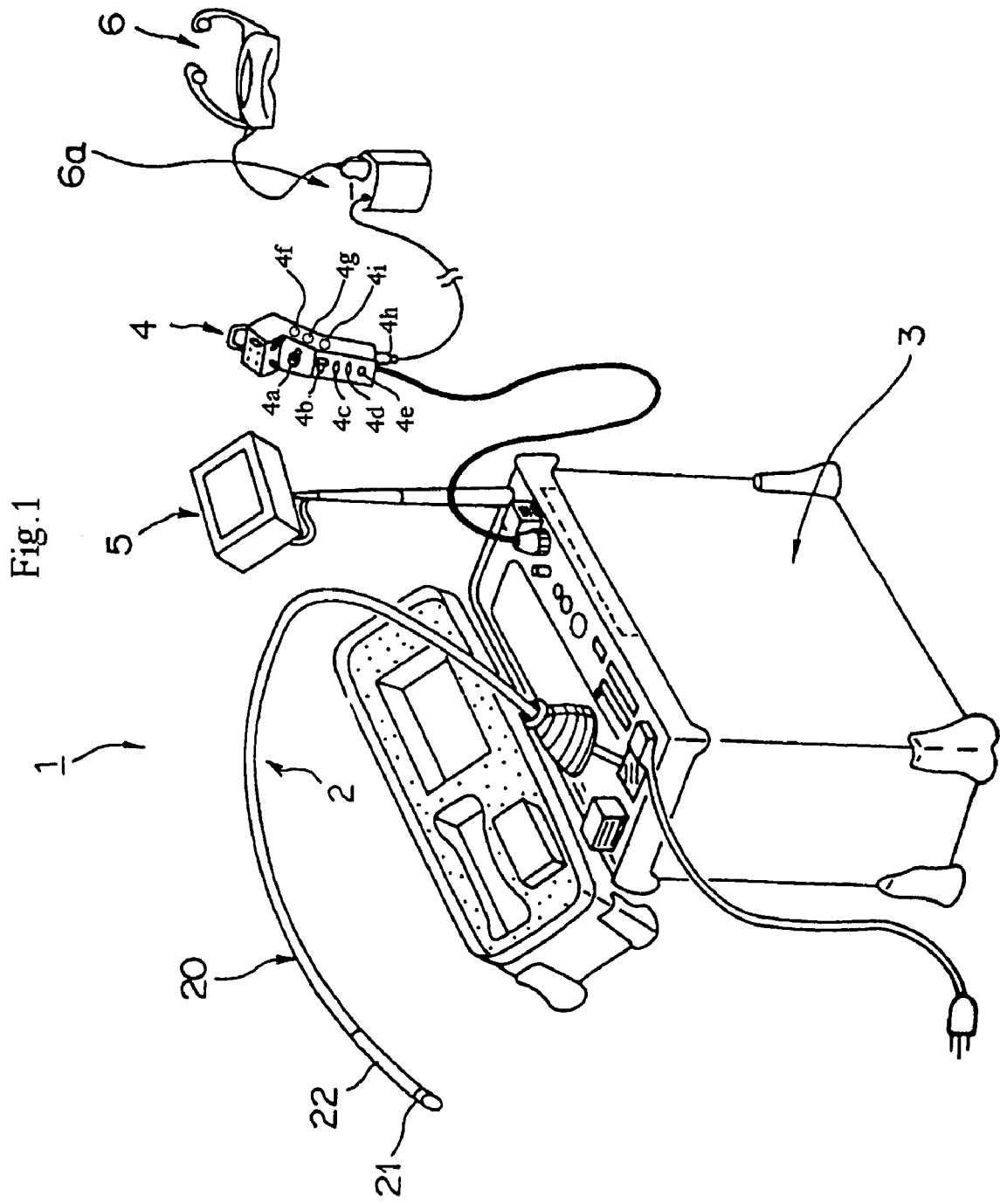

As shown in FIG. 1, an endoscope apparatus according to Embodiment 1 of the present invention primarily includes: an endoscope 2 having an insertion section 20 which is elongated and interchangeable; a control unit 3 which is a control device provided with an accommodation portion for accommodating the insertion section 20 of the endoscope 2; a remote controller 4 for performing an operation necessary for executing various operation controls of the entire device; a liquid crystal display monitor (hereinafter referred to as an LCD) 5 which is a display device for displaying an endoscope image and/or a content of operational control (for example, processing menu) or the like; a face-mounted display (hereinafter referred to as a FMD) 6 for enabling three-dimensional view of a normal endoscope image or a pseudo-stereo image of the endoscope image; and a FMD adapter 6a for supplying image data to the FMD 6.

Figure 3:
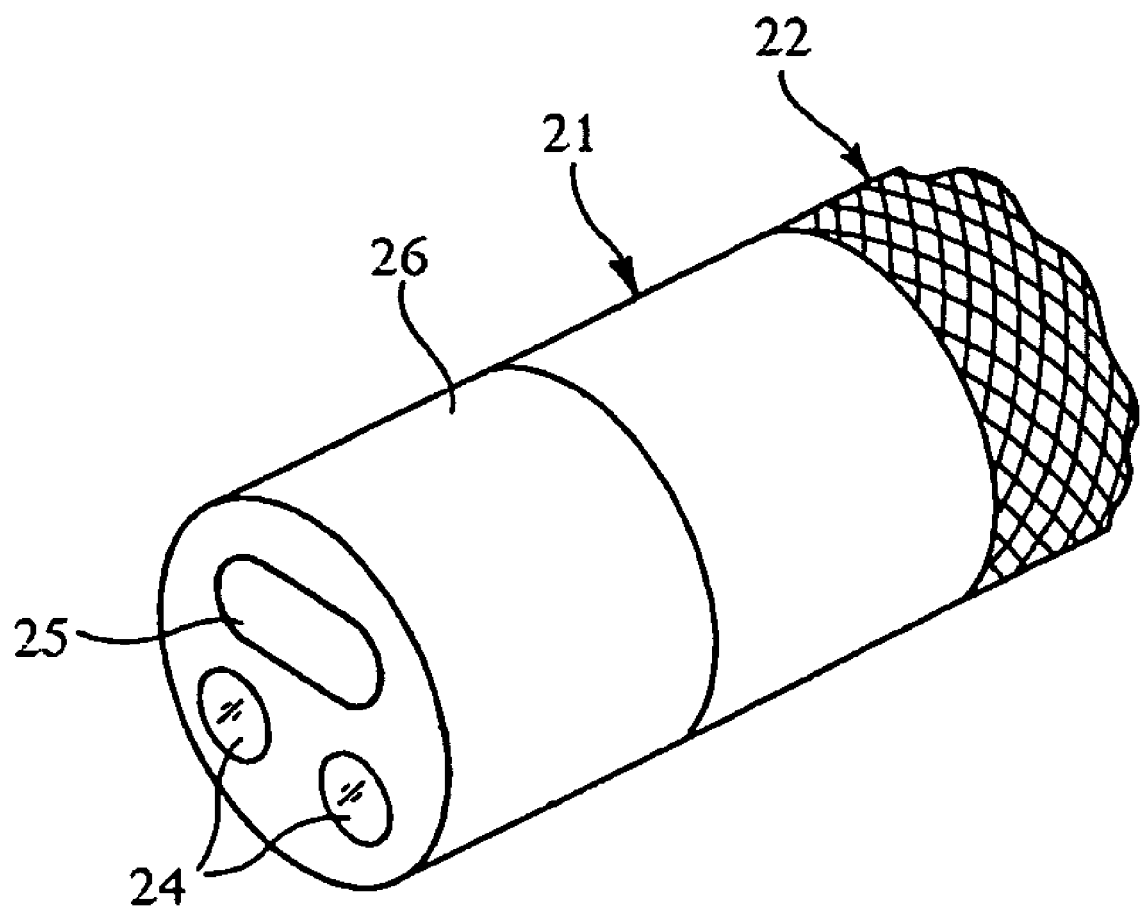

The insertion section 20 includes a rigid distal end portion 21, a bending portion 22 which can be bent in, for example, up, down, left, and right directions, and an interchangeable tube portion 23 which has flexibility. These portions are concatenated in that order from the distal end. The distal end portion 21 contains a CCD (optical image pickup element, not shown) and is adapted to be freely attachably and detachably coupled to an optical adapter 26 capable of three-dimensional observation and stereo measurement or to an optical adapter for comparative measurement (not shown) for use in normal observation. The optical adapter 26 is provided with two observation windows 24 and an illuminating window 25 as shown in FIG. 3.

With respect to the three-dimensional observation and stereo measurement, not only a technique for obtaining an observation image with parallax through the two observation windows 24, but also a technique for obtaining an observation image with parallax by providing a prism between one of the observation windows 24 and the CCD may be employed.

Figure 2:
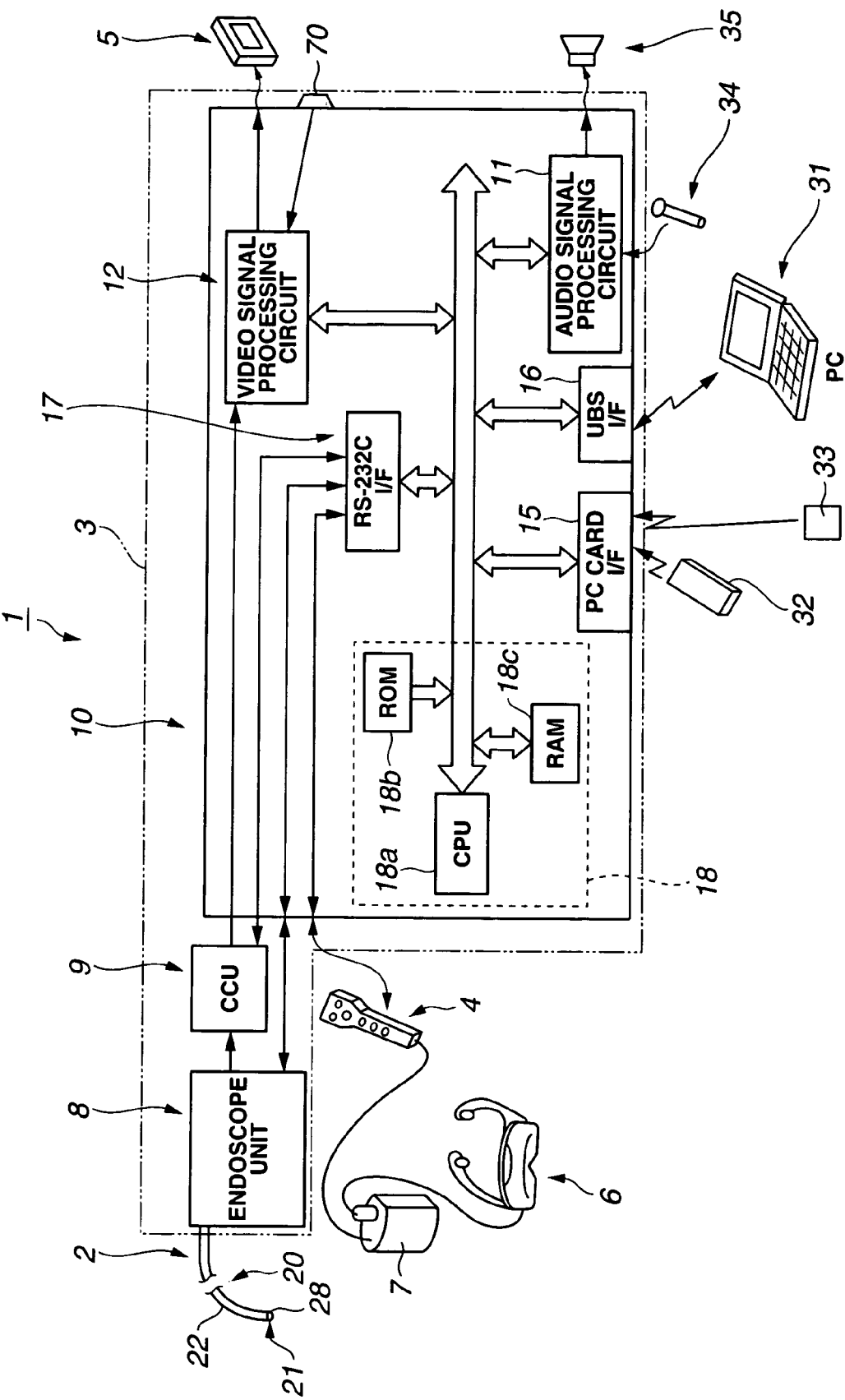

As shown in FIG. 2, the control unit 3 includes an endoscope unit 8, a camera control unit (hereinafter referred to as a CCU) 9 which is an image generating portion for performing processing for generating a video signal, and a control unit 10 for performing measurement control or the like. The proximal end of the insertion section 20 is connected to the endoscope unit 8.

The endoscope unit 8 is configured to have a light source device (not shown) for supplying illuminating light necessary for observation and a bending device (not shown) for bending the bending portion 22 which constitutes the insertion section 20.

The CCU 9 is input with a picked-up image signal which is output from an optical image pickup element contained in the distal end portion 21 of the insertion section 20. The picked-up image signal is processed and converted into a video signal such as a NTSC signal, for example, within the CCU 9, and supplied to the control unit 10.

The control unit 10 includes an audio signal processing circuit 11, a video signal processing circuit 12 to which the video signal is input, a ROM 18*b*, a RAM 18*c* which is an original image recording portion, a PC card interface (hereinafter referred to as a PC card I/F) 15 which is an image recording/reproducing portion, a USB interface (hereinafter referred to as a USB I/F) 16, and an RS-232C interface (hereinafter referred to as an RS-232C I/F) 17 etc. Within the control unit 10, each of these components is interconnected via a bus with a CPU 18*a* which executes functions of the components on the basis of a main program to perform operation control and also forms an image processing section 18 for performing image processing and measurement processing.

This image processing section 18 includes the CPU 18*a* for performing image processing and measurement processing, the ROM 18*b* in which an operation program of the CPU 18*a*, etc., is stored, and a RAM 18*c* as a memory which is used as a work area of the CPU 18*a* and also used in storing necessary data, for example. Each of these components is connected to the bus.

The RS-232c I/F 17 is connected to the CCU 9, the endoscope unit 8, and the remote controller 4 which performs control and operation instruction on the CCU 9, the endoscope unit 8, etc.

This enables a communication necessary for performing operation control on the CCU 9 and the endoscope unit 8, on the basis of an operation of the remote controller 4.

The USB I/F 16 is an interface for electrically connecting the control unit 3 to a personal computer 31. The connection between the control unit 3 and the personal computer 31 via the USB I/F 16 enables the personal computer 31 to perform various instruction controls, such as a display instruction for an endoscope image and image processing for measurement. The connection also enables an input and an output of data and control information necessary for various processing to be performed between the control unit 3 and the personal computer 31.

The PC card I/F 15 is configured such that a so-called memory card equivalent to a recording medium such as a PCMCIA memory card 32 and a compact flash® memory card 33 can be freely mounted and unmounted thereto.

By mounting the memory cards 32 and 33 to the PC card I/F 15, the control performed by the CPU 18 enables fetching of data, such as control processing information and image information stored in the memory cards 32 and 33, or recording of data, such as control processing information and image information, on the memory cards 32 and 33.

The video signal processing circuit 12 performs composition processing on a video signal fed from the CCU 9 and a display signal based on an operation menu generated under the control of the CPU 18*a* and performs processing necessary for display on the LCD 5 monitor, or the like, so that the signals are supplied to the LCD 5. Thus, a composite image of an endoscope image supplied from the CCU 9 and a graphic operation menu is displayed.

In addition, the image signal processing circuit 12 can perform processing for displaying an image singly such as an endoscope image, an operation menu, etc.

Thus, the LCD 5 monitor displays an endoscope image, an operation menu image, a composite image of an endoscope image and an operation menu image, etc.

When an instructing operation for image correction is performed, a video signal which is fed from the CCU 9 and output to the video signal processing circuit 12 is converted into a digital signal in an A/D converter (not shown) included in the video signal processing circuit 12. The digital signal is fetched into the CPU 18*a*, which constitutes the image processing section 18, for contrast correction and then converted into an analogue video signal in a D/A converter included in the video signal processing circuit 12 and output into the LCD 5. Thus, a contrast corrected image is displayed.

The audio signal processing circuit 11 is supplied with (1) an audio signal generated through sound collection of a microphone 34 and to be recorded on a recording medium such as a memory card, (2) an audio signal obtained through reproduction from a recording medium such as a memory card, or (3) an audio signal generated and processed by the CPU 18*a*. The audio signal processing circuit 11 performs processing such as amplification processing necessary for reproducing any of the supplied audio signals (1) through (3) and then outputs the signal into a speaker 35. Thus, audio is output from the speaker 35.

The CPU 18*a* executes programs stored in the ROM 18*b* so as to control various circuit portions or the like for performing processing operations which are responsive to functions other than the above contrast correction processing. The CPU 18*a* thus performs operation controls of the entire system.

As shown in FIG. 1, one side of the remote controller 4 is provided with a joystick 4*a* for instructing a bending operation of the bending portion 22, a lever switch 4*b* for use in moving a pointer when operating various menus displayed as graphics and performing measurement, a freeze switch 4*c* for instructing display of a still image on the LCD 5, a store switch 4*d* for recording a still image on the memory card 33 or the like, a measurement execution switch 4*e* for use in running a measurement software, a correction instruction switch 4*f* for adjusting the brightness of a video image when a live image is displayed and performing contrast correction on an image when a still image or a recorded image is displayed, a live switch 4*g* for instructing display of a live image on the LCD 5, a connecter portion 4*h* for connecting to the FMD adapter 6*a*, a dynamic range correction switch SW4*i*, etc.

FIG. 3 is an enlarged perspective diagram of the distal end portion 21 of the insertion section 20 of the endoscope 2. As shown in FIG. 3, the distal end of the distal end portion 21 of the endoscope 2 is coupled to the optical adapter 26 capable of three-dimensional observation and stereo measurement, with which the two observation windows 24 and an illuminating window 25 are provided.

Figure 4:
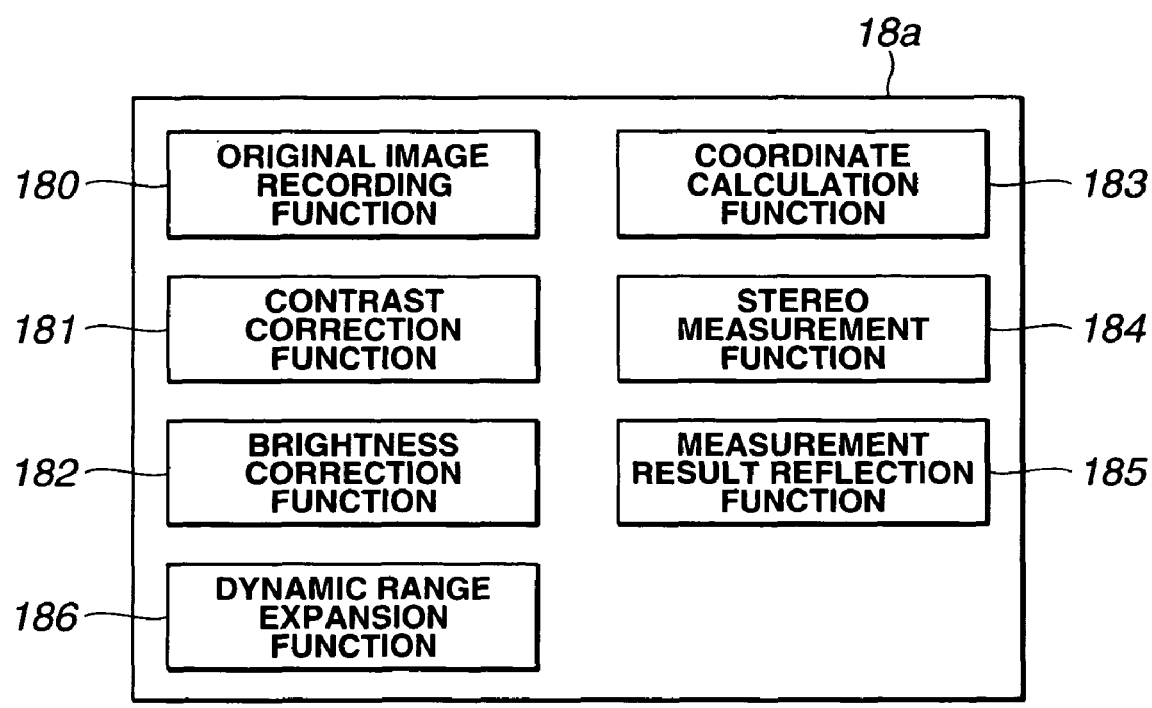

As shown in FIG. 4, the CPU 18a includes: an original image recording function 180 for recording as an original image a still image of an endoscope image (hereinafter abbreviated as a still image) or a recorded image of an endoscope image (hereinafter abbreviated as a recoded image); a contrast correction function 181 for performing contrast correction on a still image or a recorded image; a brightness correction function 182 for performing brightness correction on a live image of an endoscope image; a coordinate calculation function 183 for calculating pixel coordinates on an original image which correspond to pixel coordinates designated by the remote controller 4 on a corrected image on which contrast correction has been performed by the contrast correction function 181; a stereo measurement function 184 for performing stereo measurement using the pixel coordinates of an original image calculated by the coordinate calculation function 183; a measurement result reflection function 185 for reflecting a measurement result of stereo measurement performed by the stereo measurement function 184 on a contrast corrected image; and a dynamic range expansion function 186 for enhancing brightness of an image area which is darker than a predetermined threshold.

An operation of the present embodiment having the above configuration will be described below.

Figure 5:
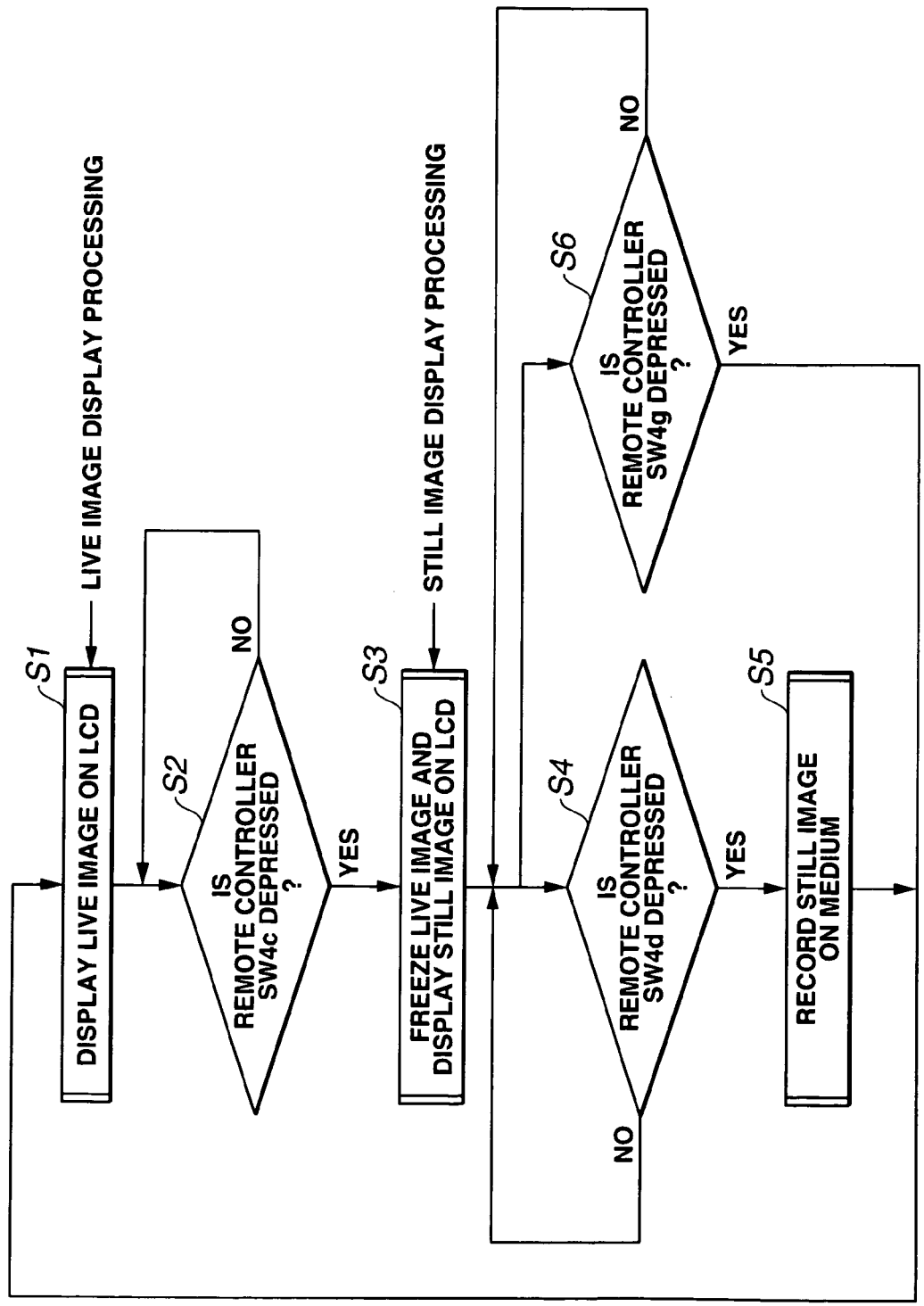

As shown in FIG. 5, in processing for displaying a still image on the LCD 5, the CPU 18a controls the video signal processing circuit 12 so as to display a live image on the LCD 5 and also executes live image display processing (to be hereinafter described) in which the brightness correction function 182 performs brightness correction on the live image, at Step S1.

Then, the CPU 18a waits for a depression of the freeze switch 4c of the remote controller 4, at Step S2. Upon the depression of the freeze switch 4c, the CPU 18a controls the video signal processing circuit 12 so as to freeze a live image and display the frozen image on the LCD 5 and also executes still image display processing (to be hereinafter described) in which the contrast correction function 181 performs contrast correction on the frozen still image, at Step S3.

Subsequently, the CPU 18a waits for a depression of the store switch 4d or the live switch 4g of the remote controller 4, at Step S4 or S6. If the store switch 4d is depressed, the CPU 18a records the still image on a medium such as the memory card 33, at Step S5, and returns to Step S1 to repeat the processing. If the live switch 4g is depressed, the CPU 18a returns to Step S1 to repeat the processing.

Figure 6:
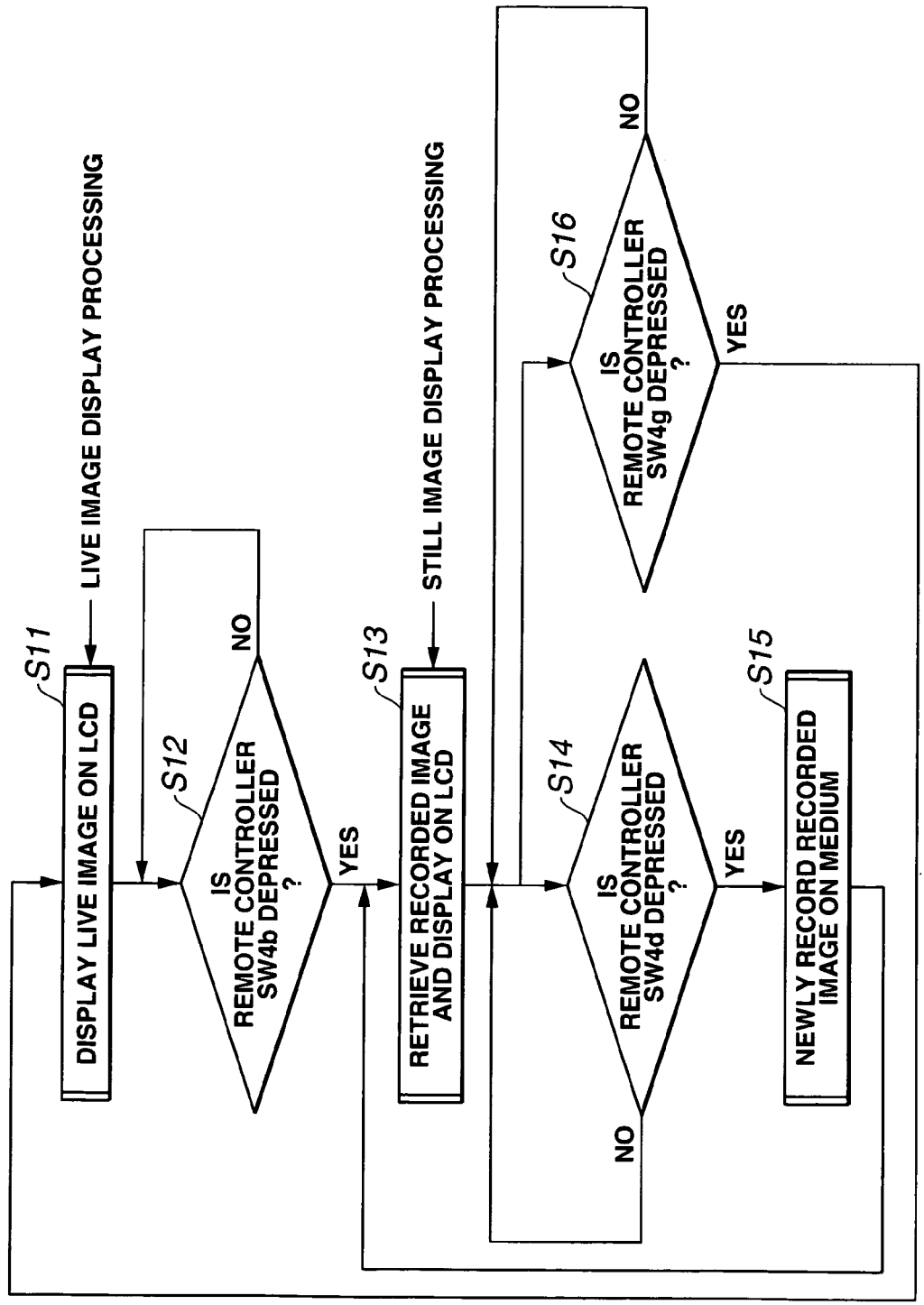

As shown in FIG. 6, in processing for displaying a recorded image on the LCD 5 which has been recorded on a medium such as the memory card 32, the CPU 18a controls the video signal processing circuit 12 so as to display a live image on the LCD 5 and also executes live image display processing (to be hereinafter described) in which the brightness correction function 182 performs brightness correction on the live image, at Step S11.

Then, the CPU 18a waits for a depression of the lever switch 4b of the remote controller 4, at Step S12. Upon the depression of the lever switch 4b, the CPU 18a reads out a recorded image recorded on the memory card 33 media and controls the video signal processing circuit 12 so as to display the recorded image on the LCD 5, and also executes recorded image display processing (to be hereinafter described) in which the contrast correction function 181 performs contrast correction on the recorded image, at Step S13.

Subsequently, the CPU 18a waits for a depression of the store switch 4d or the live switch 4g of the remote controller 4, at Step S14 or S16. If the store switch 4d is depressed, the CPU 18a newly records the brightness corrected recorded image on a media such as the memory card 32, at Step S15, and returns to Step 13 to repeat the processing. If the live switch 4g is depressed, the CPU 18a returns to Step S11 to repeat the processing.

Figure 7:
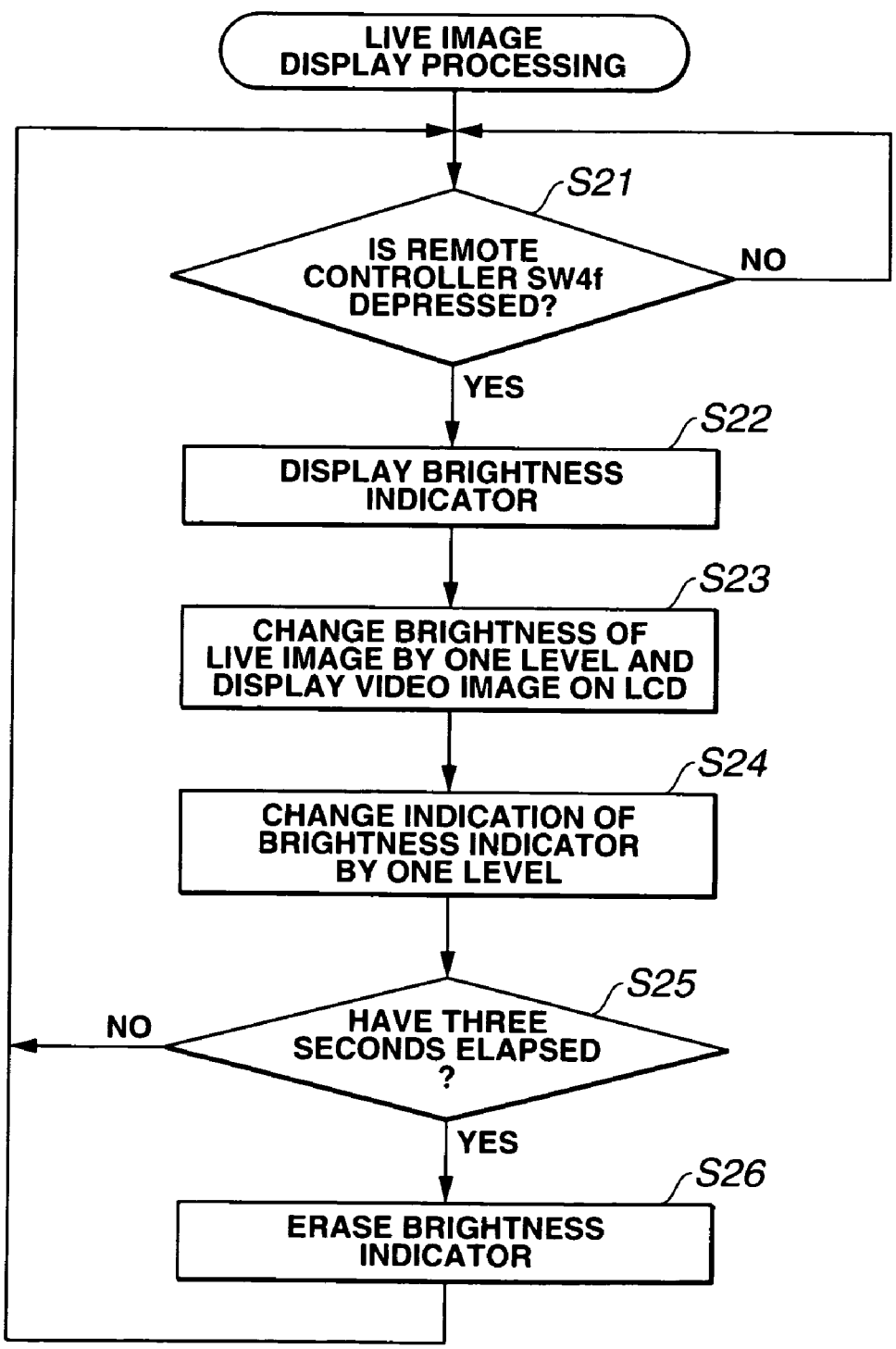
Figure 8:
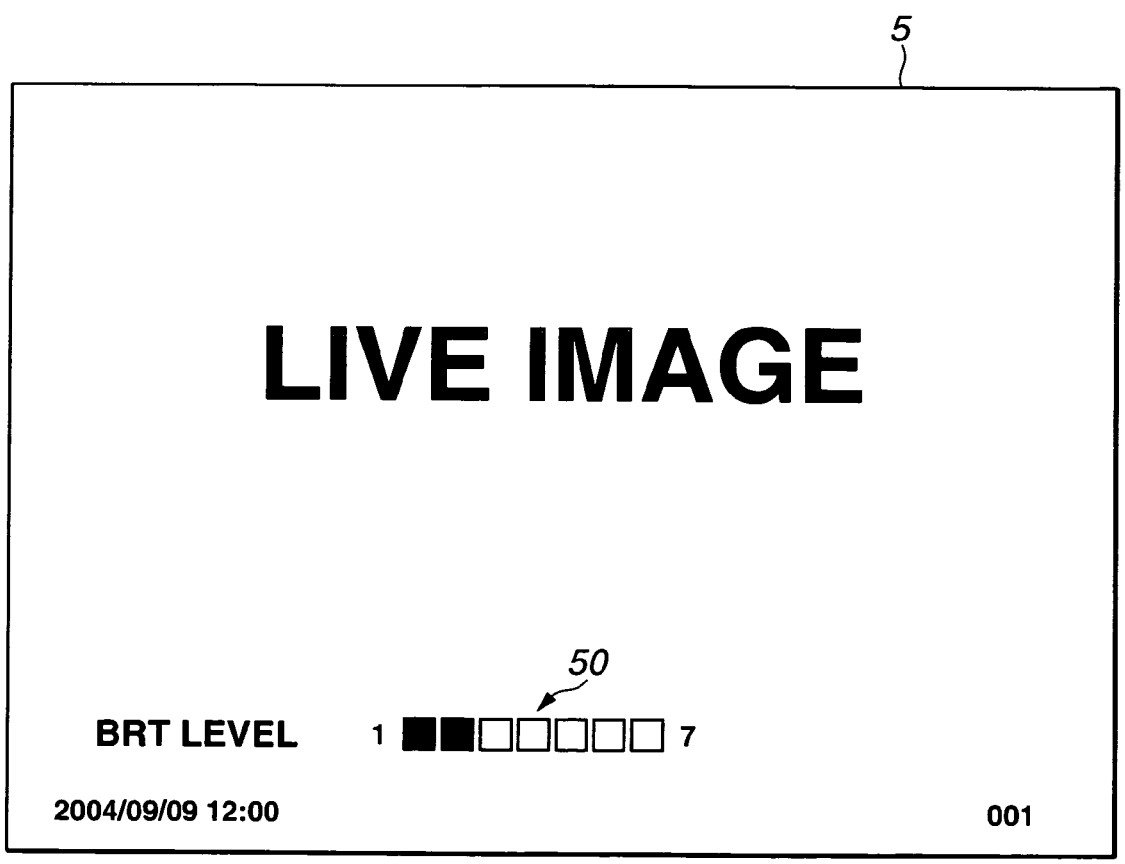

The live image display processing of Step S1 or Step S11 proceeds as shown in FIG. 7. More specifically, the CPU 18a waits for a depression of the correction instruction switch 4f of the remote controller 4, at Step S21. Upon the depression of the correction instruction switch 4f, the CPU 18a displays a brightness indicator 50 on the live image being displayed on the LCD 5 as shown in FIG. 8, at Step S22.

Then, the CPU 18a changes the brightness of the live image by one level and displays the changed video image on the LCD 5, at Step S23. At Step S24, the CPU 18a changes the indication of the brightness indicator 50 by one level.

At Step S25, the CPU 18a performs monitoring for three seconds, for example, to determine whether or not a depression of the correction instruction switch 4f occurs. If the correction instruction switch 4f is depressed within the monitoring period, the CPU 18a returns to Step S21. If the monitoring period for a depression of the correction instruction switch 4f has elapsed, the CPU 18a ceases display of the brightness indicator 50 at Step S26 and then returns to Step S21.

Figure 9:
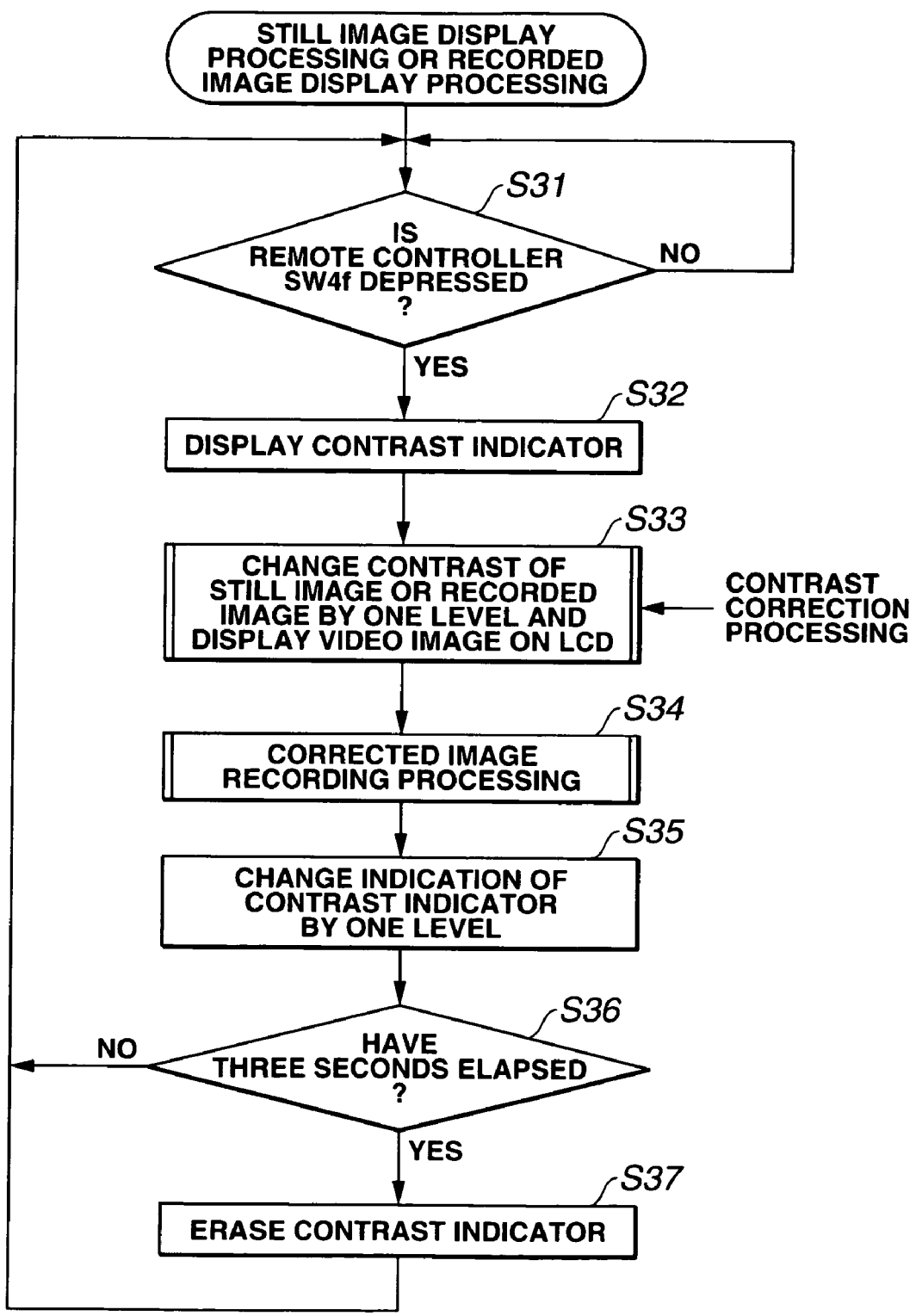

The still image display processing of Step S3 or the recorded image display processing of Step S13 proceeds as shown in FIG. 9. More specifically, the CPU 18a waits for a depression of the correction instruction switch 4f of the remote controller 4, at Step S31. Upon the depression of the correction instruction switch 4f, as shown in FIG. 10, the CPU 18a displays a contrast indicator 51 on a still image or a recorded image being displayed on the LCD 5, at Step S32.

Then, the CPU 18a changes the contrast of the still image or the recorded image by one level and performs contrast correction processing (to be hereinafter described) for displaying the changed video image on the LCD 5, at Step S33. The CPU 18a executes corrected image recording processing (to be hereinafter described), at Step S34, and then changes the indication of the contrast indicator 51 by one level, at Step S35.

At Step S36, the CPU 18a performs monitoring for three seconds, for example, to determine whether or not a depression of the correction instruction switch 4f occurs. If the correction instruction switch 4f is depressed within the monitoring period, the CPU 18a returns to Step S31. If the monitoring period for a depression of the correction instruction switch 4f has passed, the CPU 18a ceases the display of the contrast indicator 51 at Step S37 and then returns to Step S31.

Figure 11:
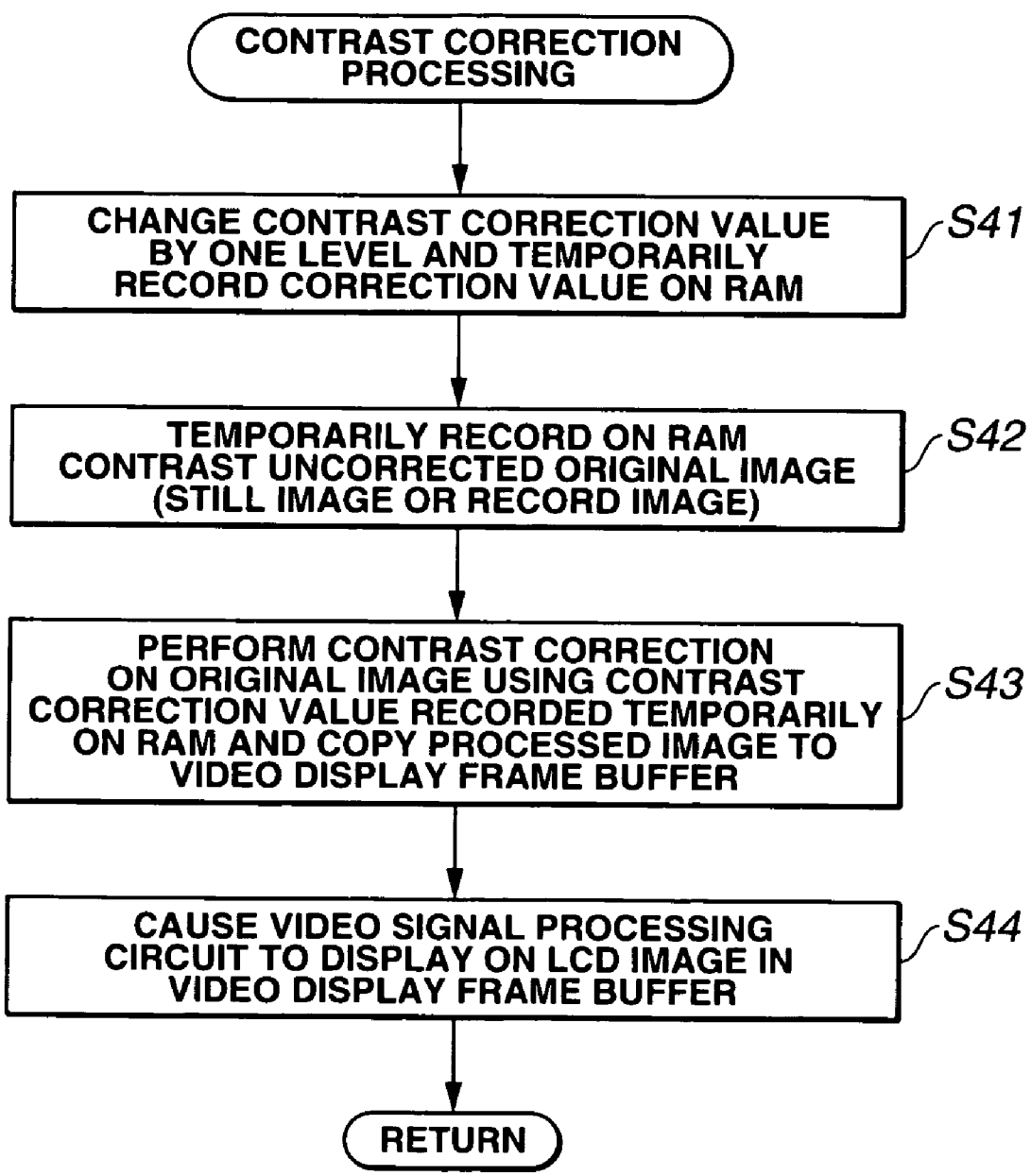

The contrast correction processing of Step S33 proceeds as shown in FIG. 11. More specifically, the CPU 18a changes a contrast correction value by one level and temporarily records the changed correction value on the RAM 18c, at Step S41. At Step S42, the CPU 18a temporarily records the contrast uncorrected original image (still image or recorded image) on the RAM 18c.

Then, the CPU 18a performs contrast correction on the original image (still image or recorded image) using the contrast correction value recorded temporarily on the RAM 18c and controls the video signal processing circuit 12 so as to copy the processed image to a video display frame buffer (not shown) included in the video signal processing circuit 12, at Step S43.

Subsequently, the CPU 18a controls the video signal processing circuit 12 so as to display on the LCD 5 the image in the video display frame buffer at Step S44 and then terminates the processing.

Figure 12:
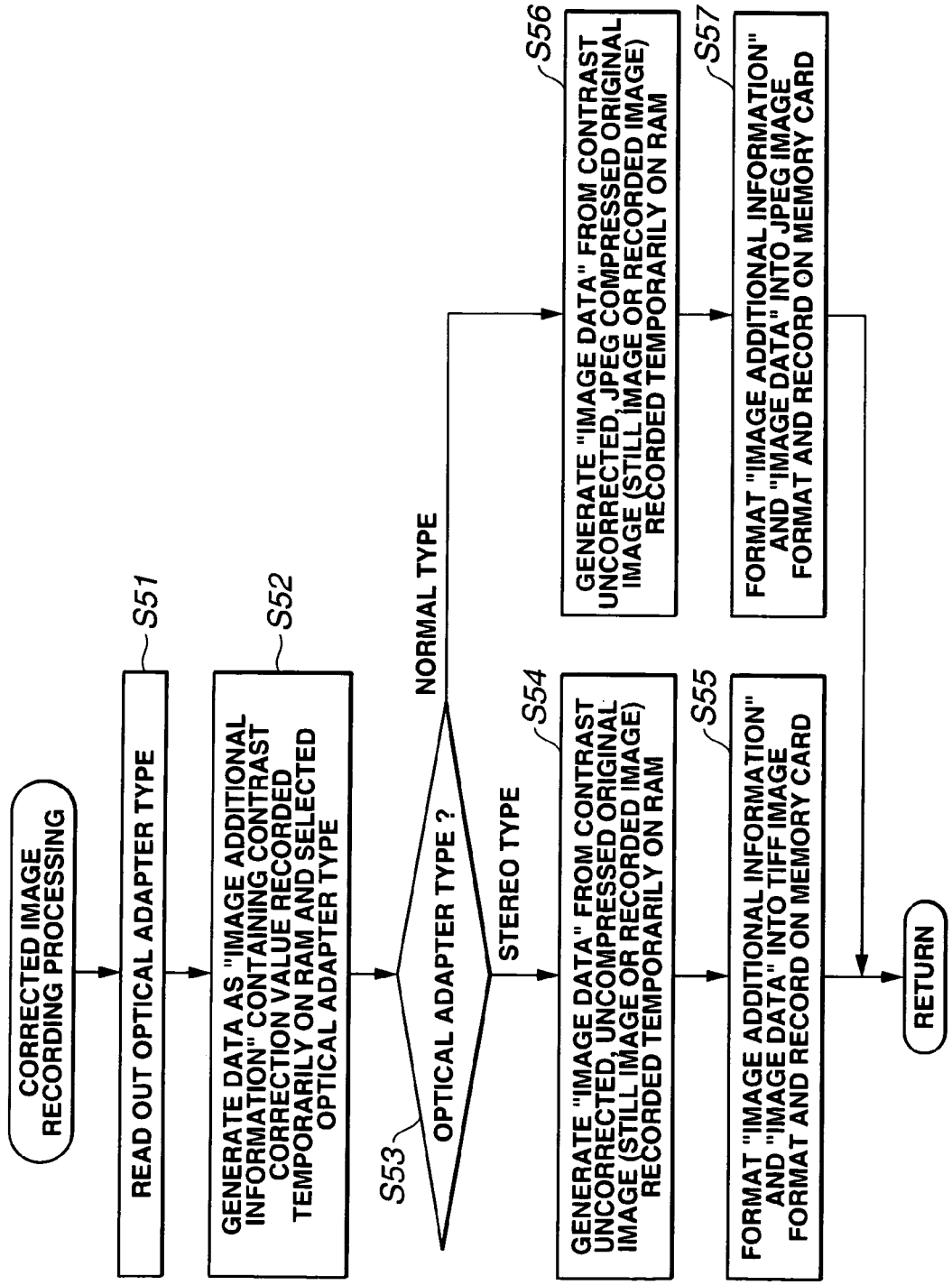

The corrected image recording processing of Step S34 proceeds as shown in FIG. 12. More specifically, the CPU 18a reads out optical adapter type information of the optical adapter 26 which is prestored in the RAM 18c, at Step S51. At Step S52, the CPU 18a generates data as "image additional information" which contains the contrast correction value recorded temporarily on the RAM 18c and the read-out optical adapter type information.

Then, the CPU 18a determines whether the optical adapter type information indicates a stereo type or a normal type, at Step S53. If the adapter type is the stereo type, the CPU 18a generates "image data" from the contrast uncorrected original image (still image or recorded image) temporarily recorded on the RAM 18c, without performing a compression operation, at Step S54. The CPU 18a formats the "image additional information" and the "image data" into TIFF image format and records the formatted data on the memory card 33, at Step S55, and then terminates the processing.

If the optical adapter type information indicates the normal type (monocular type), the CPU 18a performs JPEG compression on the contrast uncorrected original image (still image or recorded image) recorded temporarily on the RAM 18c and generates "image data" from the contrast uncorrected, JPEG compressed image, at Step S56. The CPU 18a formats the "image additional information" and the "image data" into JPEG image format and records the formatted data on the memory card 33, at Step S57, and then terminates the processing.

Figure 13:
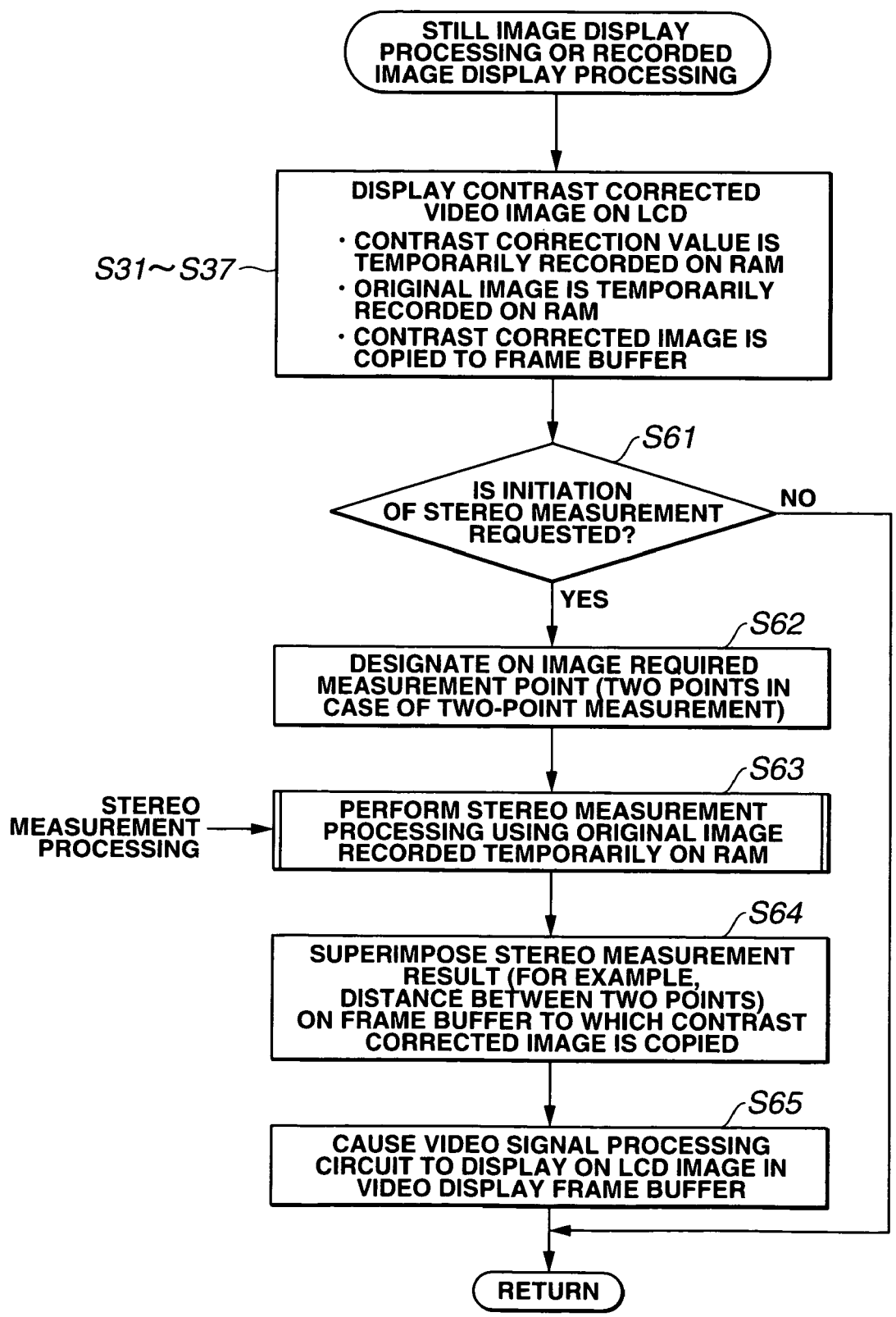

The above-described still image display processing or the recorded image display processing shown in FIG. 9 is processing performed when stereo measurement is not performed. However, if the measurement execution switch 4e of the remote controller 4 is depressed during the still image display processing or the recorded image display processing, still image display processing or recorded image display processing as shown in FIG. 13 is executed.

More specifically, the CPU 18a executes the processing of Step S31 through Step S37 described with reference to FIG. 9. As mentioned above, while the CPU 18a executes the processing to display a contrast corrected video image on the LCD 5, the following processing such as A1 through A3 is performed as well:

A1: a contrast correction value is temporarily recorded on the RAM 18c;

A2: an original image is temporarily recorded on the RAM 18c; and

A3: a contrast corrected image is copied to the video display frame buffer in the video signal processing circuit 12.

Under this state, if an initiation of stereo measurement is requested through a depression of the measurement execution switch 4e of the remote controller 4 at Step S61, the CPU 18a designates a required measurement point (two points in a case of two-point measurement) on the image on the LCD 5 through a depression of the remote controller 4, at Step S62.

Then, using the coordinate calculation function 183, the CPU 18a calculates pixel coordinates on the original image which correspond to the pixel coordinates designated by the remote controller 4 on the contrast corrected image and, using the stereo measurement function 184, performs stereo measurement processing using the original image recorded temporarily on the RAM 18c, at Step S63. The stereo measurement processing mentioned herein is disclosed in detail in Japanese Unexamined Patent Application Publication No. 10-248806, FIG. 9, etc. and has been heretofore known. Accordingly, the description of the processing is omitted.

Subsequently, using the measurement result reflection function 185, the CPU 18a superimposes a result of stereo measurement (for example, a distance between two points) in the video display frame buffer to which the contrast corrected image has been copied, at Step S64. The CPU 18a controls the video signal processing circuit 12, so as to display on the LCD 5 the image in the video display frame buffer at Step S65 and then terminates the processing.

According to this embodiment, as described above, when performing image correction such as contrast correction on a still image or a recorded image and displaying the corrected image on the LCD 5, the original image before correction is temporarily recorded on the RAM 18c. Thus, a measurement point for stereo measurement can be designated using a corrected image on the LCD 5, and the actual stereo measurement is executed using the original image before correction which is recorded temporarily on the RAM 18c. This brings about precise measurement without error. In addition, a measurement result is reflected on the display of the corrected image, which enables the measurement result to be confirmed on the image that facilitates observation.

Figure 14:
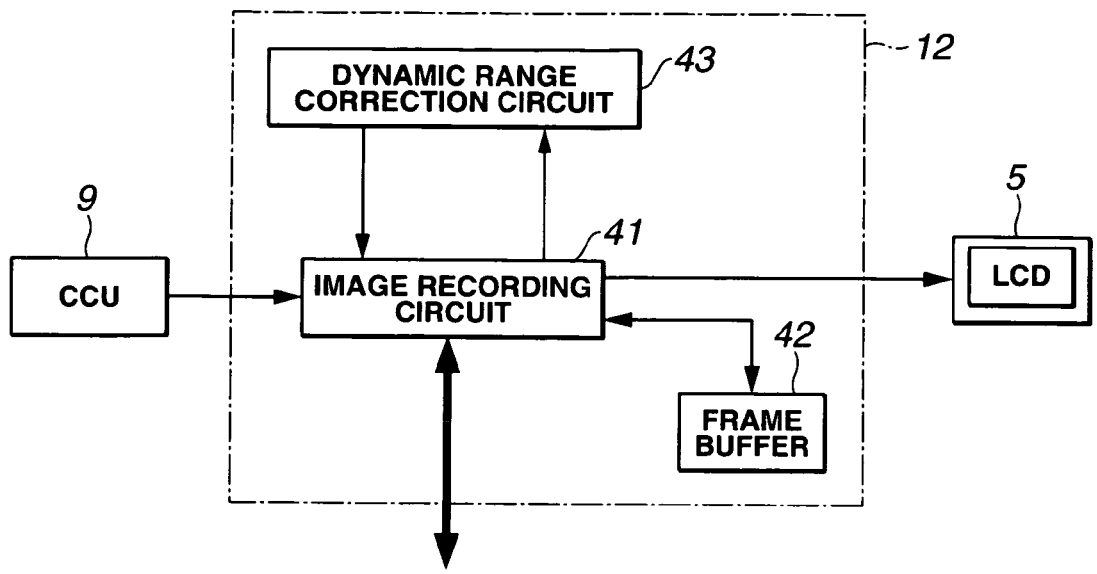

A case where correction for expanding a dynamic range is performed using the dynamic range expansion function 186 will now be described referring to FIG. 14. As shown in FIG. 14, the CPU 18a controls an image recording circuit 41, a frame buffer 42, and a dynamic range correction circuit 43, which are included in the video signal processing circuit 12, so as to implement the dynamic range expansion function 186.

The correction for expanding a dynamic range is correction for enhancing brightness on an image area which is darker than a predetermined threshold. Since only dark image area is selectively corrected, visibility can be enhanced while saturation in a light area is prevented. In addition, a dark image area to be corrected can be enlarged or reduced by changing a threshold level.

A video signal transmitted from the CCU 9 is input to the image recording portion 41. When a live image is displayed, the image recording portion 41 is arranged to output image data as it is which has been output from the CCU 9.

In processing for displaying a still image, as described with reference to the flowchart of FIG. 5, when the freeze switch SW4c is depressed at Step 2, the image recording portion 41 saves image data in the frame buffer 42 and outputs the saved image data to the LCD 5 so as to display a still image on the LCD 5.

In processing for reproducing a recorded image, as described with reference to the flowchart of FIG. 6, when the lever switch SW4b is depressed at Step 12, the image recording portion 41 saves in the frame buffer 42 image data transmitted from a medium. The image recording portion 41 outputs the image data saved in the frame buffer 42 and displays a recorded image on the LCD 5.

Figure 15:
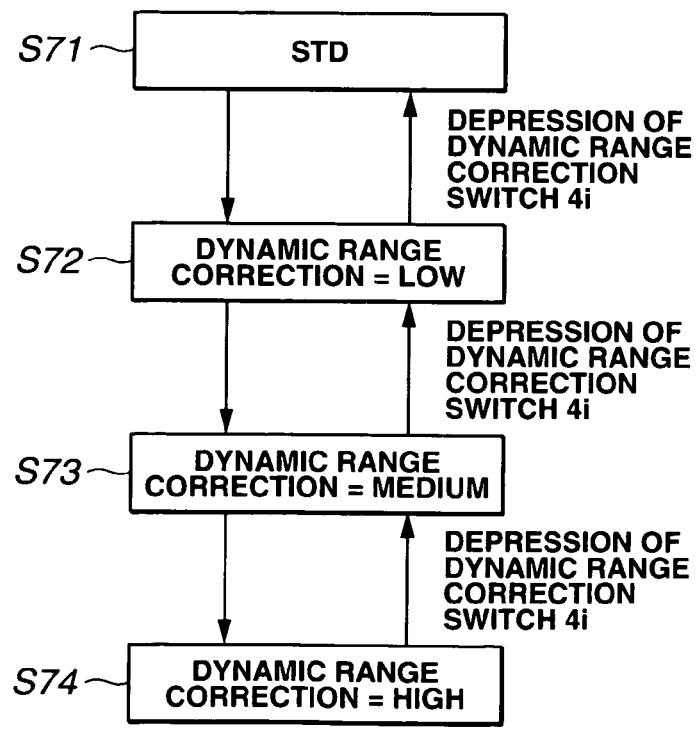
Figure 16:
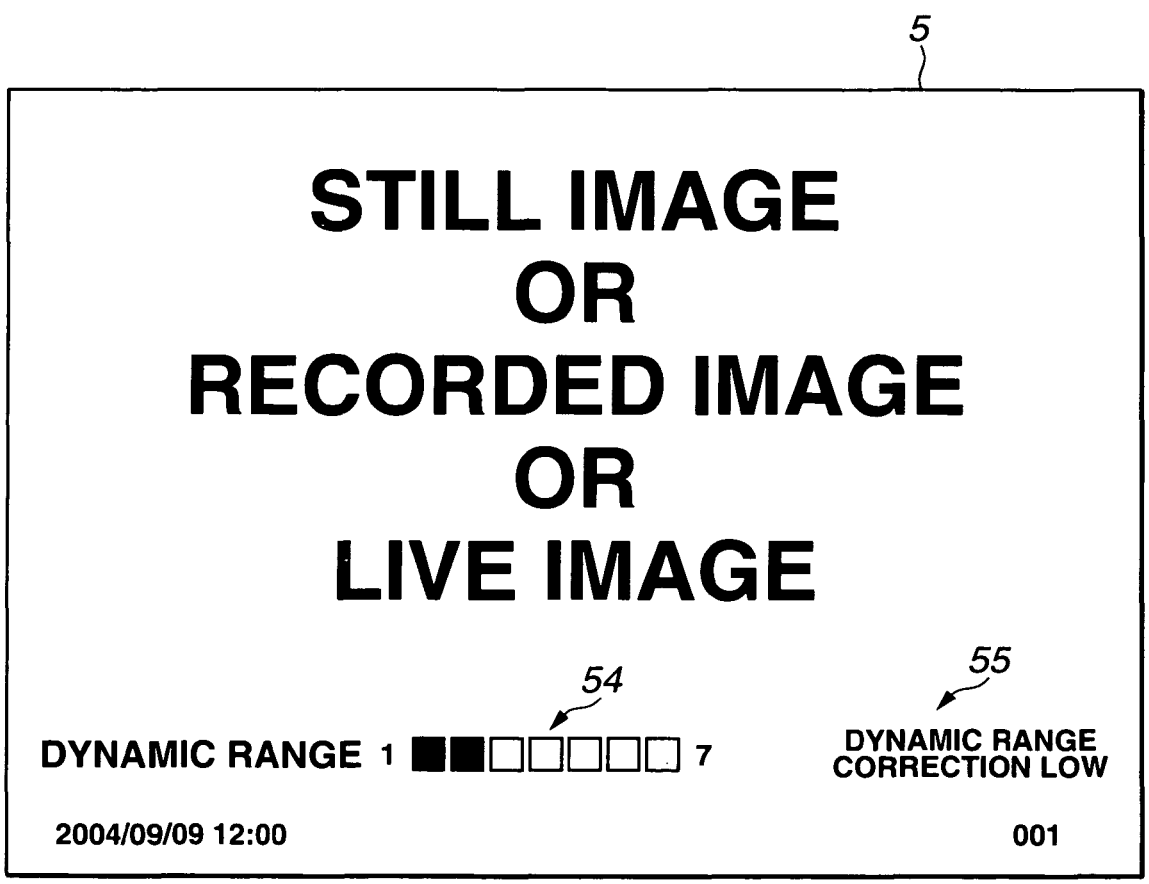

When the dynamic range correction processing is desired, the dynamic range correction switch SW4i is depressed. Upon the depression of the dynamic range correction switch SW4i, image data input in the image recording portion 41 is once input to the dynamic range correction portion 43, so that correction of dynamic range is performed. The dynamic range corrected image data is input to the image recording portion 41 and then displayed on LCD 5. As shown in FIG. 15, the dynamic range correction level can be changed, in such a way as illustrated in Step S71 through S74, through a depression the dynamic range correction switch SW4i. As shown in FIG. 16, a selected dynamic range correction level is displayed through the dynamic range indicator 54 and level text information 55.

Figure 17:
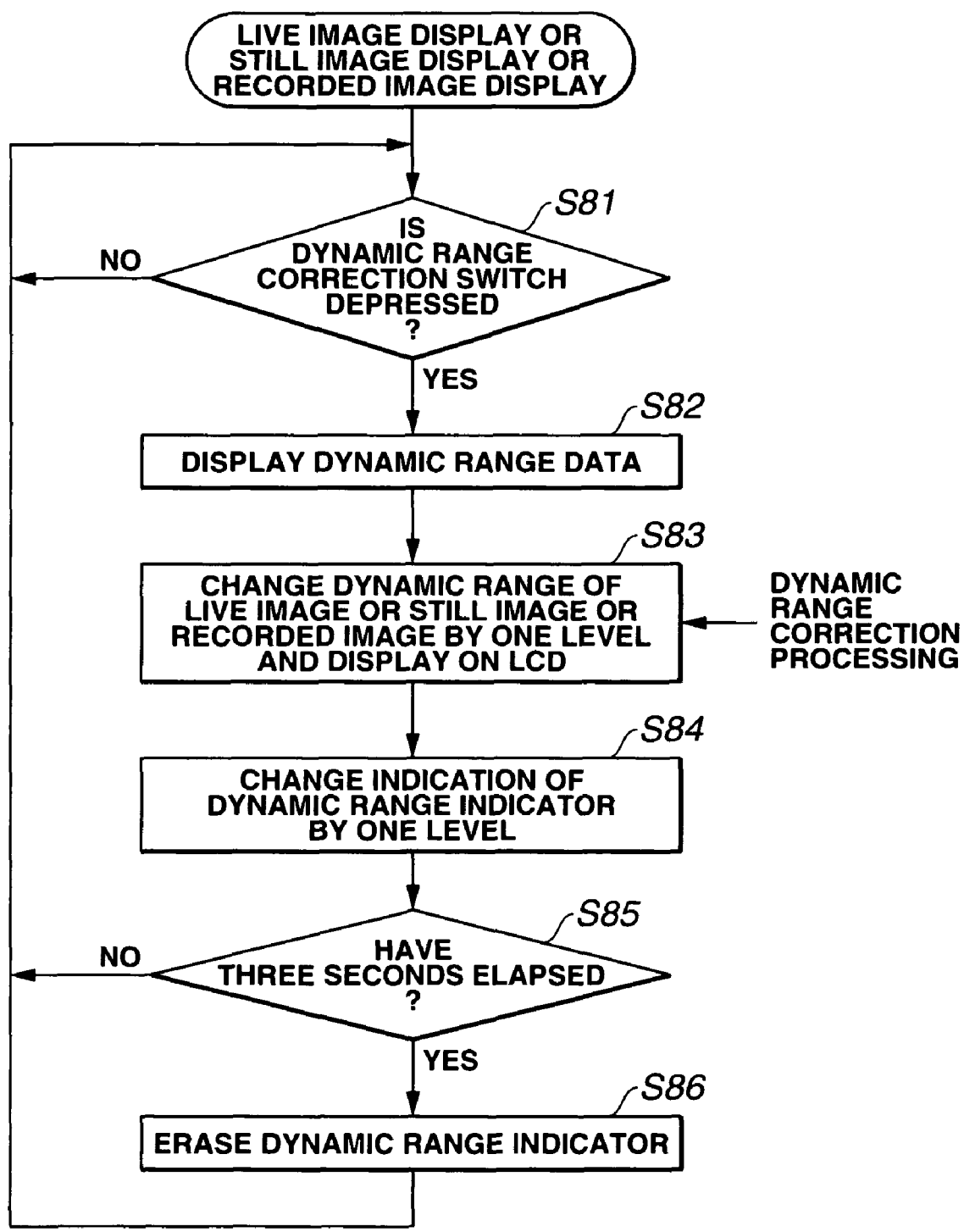

FIG. 17 shows a flowchart illustrating a case where dynamic range correction is performed. As shown in FIG. 17, the CPU 18a waits for a depression of the dynamic range correction switch SW4i of the remote controller 4, at Step S81. Upon the depression of the dynamic range correction switch SW4i, the CPU 18a displays the dynamic range indicator 54 and the level text information 55 on a live image being displayed on the LCD 5, at Step S82.

Then, the CPU 18a changes the dynamic range of the live image by one level and displays the changed video image on the LCD 5, at Step S83. At Step S84, the CPU 18a changes by one level each of the indications of the dynamic range indicator 54 and the level text information 55.

The CPU 18a performs monitoring for three seconds, for example, to determine whether or not a depression of the dynamic range correction switch SW4i occurs, at Step S85. If the dynamic range correction switch SW4i is depressed within the monitoring period, the CPU 18a returns to Step S81. If the monitoring period for a depression of the dynamic range correction switch SW4i has elapsed, the CPU 18a ceases the display of the dynamic range indicator 54 and the level text information 55, at Step S86, and then returns to Step S81.

Figure 18:
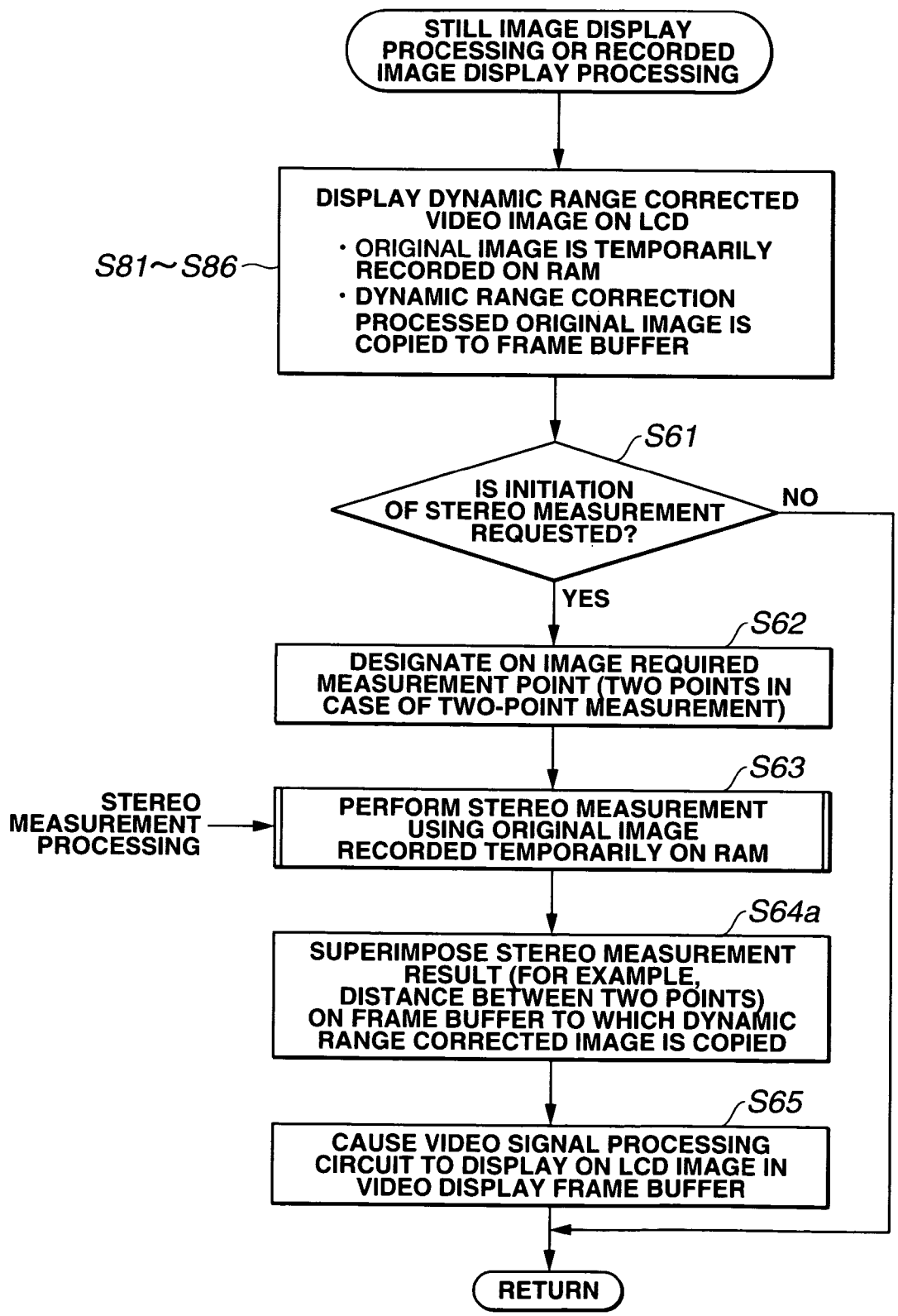

FIG. 18 shows a flowchart illustrating a case where dynamic range correction processing is performed in stereo measurement. This processing is largely similar to the processing described with reference to FIG. 13. As shown in FIG. 18, the CPU 18a first executes the processing of Step S81 through S86 described with respect to FIG. 17. As mentioned above, while the CPU 18a executes the processing to display a dynamic range corrected video image on the LCD 5, the following processing such as B1 and B2 is performed as well:

B1: an original image is temporarily recorded on the RAM 18c; and

B2: a dynamic range corrected image is copied to the video image frame buffer in the video signal processing circuit 12.

Under this state, if an initiation of stereo measurement is requested through a depression of the measurement execution switch 4e of the remote controller 4 at Step S61, the CPU 18a designates a required measurement point (two points in a case of two-point measurement) on the image on the LCD 5 through the depression of the remote controller 4, at Step S62.

Then, using the coordinate calculation function 183, the CPU 18a calculates pixel coordinates on the original image which correspond to pixel coordinates designated by the remote controller 4 on the dynamic range corrected image and, using the stereo measurement function 184, performs stereo measurement processing using the original image recorded temporarily on the RAM 18c, at Step S63.

Subsequently, using the measurement result reflection function 185, the CPU 18a superimposes a result of stereo measurement (for example, a distance between two points) on the video display frame buffer to which the dynamic range corrected image has been copied, at Step S64a. The CPU 18a controls the video signal processing circuit 12, so as to display on the LCD 5 the image in the video display frame buffer, at Step S65, and then terminates the processing.

This invention is not limited to the foregoing embodiment, and various changes and modifications may be made within a scope that does not change the gist of the present invention.

For example, the foregoing embodiment is described by way of example in which the embodiment is applied to an apparatus according to the present invention which performs contrast correction on a still image or a recorded image and brightness correction on a live moving image of an endoscope image. However, the embodiment is not limited to this example, and can advantageously be applied to an apparatus which has an arrangement for performing correction on image displayed on a display section.

Moreover, the foregoing embodiment has a configuration in which the endoscope apparatus contains a control unit therein having an arrangement according to the present invention. However, the embodiment is not limited to this configuration, and the unit may be configured as a separate unit in accordance with a type of usage.

In the invention, other embodiments that vary over a wide range can be configured on the basis of the present invention without departing from the spirit and the scope of the invention. The invention is not limited to a specific embodiment thereof except as defined in the appended claims.

The invention claimed is:

1. An endoscope apparatus comprising:
an endoscope for picking up an image signal;
an image generating portion for generating an image from the image signal picked up by the endoscope;
an original image recording portion for temporarily recording the image generated by the image generating portion as an original image;
an image correcting portion for performing image correction on the image generated by the image generating portion to generate a corrected image;
a display device for displaying the corrected image;
a measurement point designating portion for designating a measurement point on the corrected image displayed on the display device; and
a measurement portion for transforming a pixel coordinate of the measurement point designated on the corrected image to a corresponding pixel coordinate on the original image, and performing measurement processing on the original image temporarily recorded by the original image recording portion using the corresponding pixel coordinate on the original image.

2. The endoscope apparatus of claim 1, wherein the image correcting portion perform at least one of contrast correction, correction for expanding a dynamic range, and brightness correction on the image generated by the image generating portion.

3. The endoscope apparatus of claim 1, wherein the image correcting portion includes a correction information notifying portion for notifying an image correction information.

4. The endoscope apparatus of claim 3, wherein the correction information notifying portion superimposes the image correction information on the corrected image to perform notification.

5. The endoscope apparatus of claim 4, wherein the image correction information to be superimposed is indicator information.

6. An endoscope apparatus comprising:
an image recording portion for storing on a recording medium an image picked up by an endoscope;
an image correcting portion for performing image correction on the image read out from the recording medium to generate a corrected image;
a display device for displaying the corrected image;
a measurement point designating portion for designating a measurement point on the corrected image displayed on the display device; and
a measurement portion for transforming a pixel coordinate of the measurement point designated on the corrected image to a corresponding pixel coordinate on the image stored in the recording medium, and performing measurement processing on the image stored in the recording medium using the corresponding pixel coordinate on the image stored in the recording medium.

7. The endoscope apparatus of claim 6, wherein the image correcting portion performs at least one of contrast correction, correction for expanding a dynamic range, and brightness correction on the image read out from the recording medium to generate the corrected image.

8. The endoscope apparatus of claim 6, wherein the image correcting portion includes a correction information notifying portion for notifying an image correction information.

9. The endoscope apparatus of claim 8, wherein the correction information notifying portion superimposes the image correction information on the corrected image to perform notification.

10. The endoscope apparatus of claim 9, wherein the image correction information to be superimposed is indicator information.

* * * * *